United States Patent [19]

Williams

[11] Patent Number: 5,300,127

[45] Date of Patent: Apr. 5, 1994

US005300127A

[54] SEED COATINGS

[75] Inventor: Paul M. Williams, Luton, England

[73] Assignee: Agricultural Genetics Company Limited, Cambridge, England

[21] Appl. No.: 830,920

[22] Filed: Feb. 4, 1992

Related U.S. Application Data

[60] Division of Ser. No. 759,624, Sep. 16, 1991, Pat. No. 5,106,648, which is a continuation of Ser. No. 459,313, Dec. 29, 1989, abandoned.

[30] Foreign Application Priority Data

Jan. 6, 1989 [GB] United Kingdom ................. 8900313

[51] Int. Cl.$^5$ ........................ A01C 1/06; A01C 21/00; C05F 11/08; C05G 5/00
[52] U.S. Cl. ................................ 47/57.6; 47/DIG. 9; 47/DIG. 11; 71/6; 71/7; 71/64.07; 71/64.08; 71/904; 424/93 D; 427/3; 427/4; 427/214; 427/221; 504/100; 504/101
[58] Field of Search ......... 47/57.6, DIG. 9, DIG. 11, 47/56, 57.601, 57.604, 57.605, 57.612, 57.618, 57.617, 57.615; 424/93 D; 427/3, 4, 214, 221; 71/64.08, 64.07, 904, 6, 7; 504/100, 101

[56] References Cited

U.S. PATENT DOCUMENTS

| | | | |
|---|---|---|---|
| 4,249,343 | 2/1981 | Dannelly | 47/57.6 |
| 4,272,417 | 6/1981 | Barke et al. | 47/57.6 |
| 4,344,979 | 8/1982 | Gago et al. | 427/4 |
| 4,367,609 | 1/1983 | Lloyd | 47/57.6 |
| 4,438,593 | 3/1984 | McNew et al. | 47/57.6 |
| 4,583,320 | 4/1986 | Redenbaugh | 47/57.6 |
| 4,779,376 | 10/1988 | Redenbaugh | 47/57.6 |
| 4,828,600 | 5/1989 | McCabe et al. | 47/57.6 |
| 4,849,005 | 7/1989 | Williams et al. | 71/7 |

FOREIGN PATENT DOCUMENTS

| | | |
|---|---|---|
| 0010630 | 5/1980 | European Pat. Off. |
| 0134634 | 3/1985 | European Pat. Off. |
| 0192342 | 8/1986 | European Pat. Off. |
| 0253673 | 1/1988 | European Pat. Off. |
| 2080669 | 2/1982 | United Kingdom |

Primary Examiner—Howard J. Locker
Attorney, Agent, or Firm—Oblon, Spivak, McClelland, Maier & Neustadt

[57] ABSTRACT

The invention relates to a soybean seed, lucerne seed or clover seed coated with an inoculant composition comprising a carrier medium, a beneficial microorganism and an adhesive polymeric material. A high average loading of viable organisms per seed is maintained in storage.

24 Claims, No Drawings

SEED COATINGS

This is a division of application Ser. No. 07/759,624, filed on Sep. 16, 1991, now U.S. Pat. No. 5,106,648, which is a continuation of Ser. No. 07/459,313, filed on Dec. 29, 1989, now abandoned.

The invention relates to seed coatings, and more particularly to methods for the inoculation of agriculturally useful seeds with beneficial microorganisms. The term microorganism is used broadly in this specification to denote bacteria, fungi and higher or lower organisms.

Certain microorganisms can function in a number of ways to improve growth of the plants, to improve N and P status of plants or to control certain pests and diseases which affect plants. These organisms include bacteria of the genera Rhizobium (including Bradyrhizobium), Pseudomonas, Serratia, Bacillus, Pasteuria, Azobacter, Enterobacter, Azospirillum, and Cyanobacteria, (blue-green algae), fungi of the genera Gliocladium, Trichoderma, Coniotherium, Verticillium, Paecilomyces, Metarhizium, and mycorrhizal fungi, and entomophilic nematodes when present in the soil in the vicinity of the roots of particular plants. The microorganisms to be used are generally introduced into the soil at sowing by the use of inoculant compositions. The inoculant is placed in intimate contact with the seed normally by either dry, moist or slurry inoculation techniques. In slurry inoculation, the inoculant is mixed with water and generally an adhesive e.g. gum arabic or methyl cellulose is used, to improve adhesion.

UK patent 2 080 669 proposes the use of a water-soluble polyvinyl pyrrolidone (PVP) in Rhizobium inoculatns. The water-soluble polyvinyl pyrrolidone is tated to promote the survival of the microorganism. Our prior European Patent Application No. 87 306 343. 2 discloses an inoculant composition for plants, comprising a carrier medium, a beneficial species of microorganism and a copolymer of vinyl pyrrolidone with vinyl acetate, styrene or a substituted styrene.

The on-farm practice of inoculation adds an extra step into seed planting and is therefore often disliked by farmers. Moreover, present methods for coating seeds with microorganisms have disadvantages, in that they lead to low loadings of viable microorganism and insufficient shelf-life. In commercial practice, coated seeds with a shelf-life of at least 6 months at ambient temperature are desirable.

Unlike the dry, moist and slurry inoculation methods used on the farm, preinoculation is performed by seed coaters whereby seeds are coated with formulations (usually clay based) containing microorganisms. Commercial seed coating processes usually involve a drying phase at temperatures which can adversely affect microorganism survival. Moreover, since seed is coated well in advance of sowing, the microorganisms need to remain viable, often for several months under conditions of continuous dessication. Because of the above mentioned problems, commercial preinoculation of seeds has met with little success.

For example, UK patent 2,080,669 describes a method for precoating seeds with Rhizobia which consists of the following steps. Seeds are coated with sodium caseinate, finely ground limestone and peat, dried to remove excess moisture and then mixed with a slurry of a culture of Rhizobia in a peat medium in a solution of polyvinyl-pyrrolidone in water. Finally a kaolin/lime mixture is mixed with the coated seed to absorb any excess moisture. Although this method is claimed to give 100% survival of Rhizobia, close inspection of the results quoted reveals that this is not the case. In one example 100% survival after 21 days storage was recorded but the reproducibility of results is poor. In all the other examples 0.5–19% survival of Rhizobia after 28 days storage was recorded.

Another problem with pre-inoculation of seeds with Rhizobia is achieving sufficient numbers of bacteria per seed in order to have a beneficial effect on plant growth. It is recognized that for soybean $10^5$ bacteria per seed are required, and that for lucerne $10^3$ bacteria per seed are required. Previously described methods for pre-inoculation of seeds have been unable to achieve these targets. Slurrying of seeds with an inoculant composition containing an adhesive polymer, such as a copolymer of vinyl pyrrolidone with vinyl acetate, as described in our prior European Patent Application No. 87 306 343.2, is an improvement on the prior art in that it achieves the targets of $10^5$ bacteria per soybean seed and $10^3$ bacteria per lucerne seed. However, it still leaves room for improvement in shelf-life.

Surprisingly, we have found that slurrying of seeds with an inoculant composition, e.g. as described in our prior European Patent Application No. 87 306 343.2, in the presence of a suspension of an adhesive polymer, which is added separately as an aqueous suspension during the slurrying operation, and followed by air drying at ambient temperatures, results in a coated seed product with adequate Rhizobial numbers per seed and in which sufficient Rhizobia remain viable for a period in excess of 5 months.

According to the present invention, a method of preparing coated seeds comprises slurrying seeds with an inoculant composition containing a carrier medium, at least one species of microorganism having a beneficial effect on plants which grow from the seeds, and an adhesive polymer, slurrying being effected in the presence of an aqueous suspension of an adhesive polymer; and air drying the resulting product at a temperature not greater than 30° C.

The invention provides an improved coated seed product comprising at least one seed surrounded by a coating composition comprising a carrier, a microorganism which is beneficial for the seed or for plants resulting therefrom and an adhesive polymer which is compatible with the microorganism.

The adhesive polymer is preferably selected from copolymers of vinyl pyrrolidone and vinyl acetate, poly (methyl vinyl ether) maleic anhydride copolymers, free acids of the copolymer of methyl vinyl ether and maleic anhydride, vinylpyrroldone/styrene copolymers, partially hydrolysed polyvinyl alcohols, vinyl acetate/butyl acrylate copolymers, vinyl acetate homopolymers, terpolymers, acrylic copolymers, styrene/acrylic ester-copolymers, vinyl acetate/ethylene copolymers and polyvinyl acetate. A particularly preferred polymer is a copolymer of vinyl pyrrolidone and vinyl acetate in respective proportions by weight of from 50:50 to 70:30. Preferably, the suspension contains 10–20% by weight of the copolymer. Conveniently, the adhesive polymer in the suspension may be the same as in the inoculant composition.

The carrier is preferably peat. Alternatively, vermiculite, clay, silt, graphite, talc, filter mud, coir dust, bagasse, composted corn cobs or coal dust may be used.

The microorganism is preferably selected from Rhizobium (including Bradyrhizobium), Pseudomonas, Serratia, Bacillus, Pasteuria, Azotobacter, Enterobacter, Azospirillum, Cyanobacteria, Gliocladium, Trichoderma, Coniotherium, Verticillium, Paecilomyces, Metarhizium, mycorrhizal fungi and entomophilic nematodes.

In some circumstances it may be useful to dust the coated seeds with a powdered clay in order to improve their appearance. It may also be desirable to incorporate pigments into the coated seeds in order to distinguish them from other products. We have demonstrated that both powdered clays and pigments may be included in the coated seed composition without a detrimental effect on Rhizobia. One example of a suitable clay is calcium monmorillonite, which is also known as Surrey Powder. The pigment is preferably selected from dyes such as Rhodamine B500, Methyl Violet, Blue 2313, Eosine Y, Sunset Yellow, Magenta, Blue 23123, Pigment Green 7, Tartrazine, Malachite Green, Auramine 0, Oil Yellow 21756, Green 19102 and Methylene Blue 2B, and from titanium dioxide-coated micas (lustres) such as 100 Silver Pearl, 120 Lustre Pearl, 235 Green Pearl, 300 Gold Pearl, 500 Bronze Pearl and 504 Red Pearl.

Many seeds are coated with chemical fungicides. These may also be used according to the present invention in which case it is necessary to use Rhizobial strains that are resistant to these fungicides, thus allowing seeds to be coated with fungicides and Rhizobia at the same time. The fungicides are preferably selected from metalaxyl, carbathiin and thiram.

The coated seed product according to the invention may be prepared by mixing seeds with the ingredients of the coating composition, and drying the surface of the resulting coated seed. Drying should be done at room temperature (i.e. less than 30° C.). The proportion of inoculant to seed may be selected from the range of 0.5 to 2.5% by weight, depending on the type of seed.

Coated seeds prepared by the method described herein have the following advantages:

(a) The coated seeds are free flowing.
(b) The coating has no adverse effect on germination.
(c) Very little of the coat is lost in bagging and sowing.
(d) The coated seeds maintain high numbers of viable rhizobial cells per seed during a period of at least 3 months.

The invention is illustrated by the following Examples, of which Examples 1 to 4 are comparative and Examples 5 onward illustrate the inventive method.

EXAMPLE 1

Preparation of peat-based inoculants

Selected sedge peat (Fisons) was adjusted to pH 6.5 using calcium hydroxide and calcium carbonate. This was oven dried at 60° C. and milled in a hammer mill to pass through a 0.4 mm sieve. 150 g aliquots of powdered peat were sealed into 300 gauge polythene bags and sterilized by gamma radiation (50 KGy). The packs were injected with 115 ml of a pure culture of *Bradyrhizobium japonicum*, *Rhizobium meliloti* or *R. leguminosarum* biovar trifolii, the injection hole re-sealed and the contents intimately mixed prior to incubation for seven days at 26° C. Such inoculants contain on average $5 \times 10^9$ viable cells $g^{-1}$.

Inoculants based on peat-clay mixtures (Surrey Powder, calcium monmorillonite) can be prepared by an identical method. 150 g aliquots of a powdered peat-clay mixture (25% or 50% w/w clay) were sealed into 300 gauge polythene bags and sterilised by gamma irradiation (50 KGy). The packs were injected with 115 ml of a pure culture of *B. japonicum*, *R. meliloti* or *R. leguminosarum* biovar trifolli, the injection hole re-sealed and the contents intimately mixed prior to incubation for seven days at 26°. Such inoculants contain on average $3.6 \times 10^9$ viable cells $g^{-1}$.

EXAMPLE 2

Irradiate peat packs were prepared as described in Example 1 and injected with 57.5 ml of a pure culture of *B. japonicum*, *R. meliloti* or *R. leguminosarum* biovar trifolli plus 57.5 ml of an autoclaved 10% aqueous suspension of PVP-VA-S-630 or 57.5 ml of an autoclaved 10% aqueous solution of PVP (molecular weight 44,000). PVP-VA-S-630 is a 60:40 vinyl pyrrolidone/vinyl acetate copolymer (molecular weight 700,000) which is obtainable from GAF (Great Britain) Co., Limited, Manchester. It is a spray-dried powder which can form stable emulsions in water.

Control inoculants were prepared similarly except that 57.5 ml of water was substituted for the aqueous suspension or solution of polymer. All packs were thoroughly mixed, incubated at 26° C. for seven days and stored at room temperature. Control, PVP- and PVP-VA-S-630-containing inoculants respectively containing $6 \times 10^9$, $1.7 \times 10^8$ and $4.25 \times 10^9$ rhizobia per gram at use.

Soybean seeds were inoculated with *B. japonicum* as follows:

The control inoculants were used to inoculate soybean seed in three ways:

| | |
|---|---|
| 1. | Dry - 1 g of inoculant was mixed with 300 g of seed. |
| 2. | Water slurry - 1 g of inoculant was slurried with 2 ml of water and then mixed with 300 g of seed. |
| 3. | Gum arabic slurry - 1 g of inoculant was slurried with 2 ml of a 40% aqueous solution of gum arabic (supplier - Sigma) and then mixed with 300 g of seed. |

In all treatments, inoculated seeds were held at room temperature for 30 minutes prior to the removal of unadhered inoculant by sieving.

The inoculants containing PVP or PVP-VA-S-630 were used to inoculate soybean seed in three ways:

| | |
|---|---|
| 1. | Dry - 1 g of inoculant was mixed with 300 g of seed. |
| 2. | Moist - 300 g of seed were slightly moistened with 0.3 ml of water, prior to mixing with 1 g of inoculant. |
| 3. | Slurry - 1 g of inoculant was slurried with 2 ml of water and then mixed with 300 g of seed. |

Inoculated seeds were held at room temperature for 30 minutes prior to removal of unadhered inoculant by sieving.

All seed lots were then exposed to air and held at 25° C. for an 8 day period during which rhizobial numbers per seed were determined. Results are presented in Table 1.

From Table 1 it can be seen that only the PVP-VA-S-630 inoculant allows the desired number of rhizobia per seed (i.e. in excess of $10^5$ per seed) to be achieved. Both gum arabic and PVP can be seen to confer some degree of protection to rhizobia on the seed surface in that rhizobial survival is extended in comparison to that observed in the absence of a protectant. Rhizobial survival on the seed surface is promoted further when the PVP-VA-S-630 inoculant is used, thus demonstrating the superiority of PVP-VA-S-630 over PVP and gum arabic as a protectant. Best results are obtained when seeds are slurry mixed with PVP-VA-S-630 inoculant but even in this case rhizobial survival is inadequate for a commercial coated seed product, and further improvement is required.

| Time after inoculation (days) | No. Rhizobia per seed | | |
|---|---|---|---|
| | Dry | Water Slurry | Gum Arabic Slurry |
| Control Inoculant | | | |
| 0 | 2,600 | 20,000 | 73,000 |
| 1 | 240 | 3,000 | 31,000 |
| 2 | 0 | 2,000 | 2,700 |
| 4 | 0 | 0 | 1,000 |
| 8 | 0 | 0 | 10 |
| | Dry | Moist | Slurry |
| PVP Inoculant | | | |
| 0 | 11,000 | 1,000 | 5,000 |
| 2 | 200 | 400 | 1,000 |
| 5 | 40 | 170 | 230 |
| 8 | 0 | 80 | 60 |
| PVP-VA-S-630 Inoculant | | | |
| 0 | 140,000 | 210,000 | 780,000 |
| 2 | 17,000 | 49,000 | 120,000 |
| 5 | 10,000 | 37,000 | 81,000 |
| 8 | 3,000 | 7,800 | 13,000 |

EXAMPLE 3

In view of the harshness of the test outlined in Example 2, the test applied in this Example was performed to compare protectant performance in coated seeds stored in bags.

The effect of the PVP-VA-S-630 copolymer on rhizobial survival on the seed coat, was compared to slurry inoculation with 40% aqueous solution of gum arabic and dry inoculation with conventional (control) inoculants.

100 g lots of gamma irradiated soybean seeds were dry inoculated with 1 g of conventional inoculant (prepared as described in Example 2, $9.6 \times 10^9$ rhizobia $g^{-1}$), by shaking in a sterile bottle. Others were mixed with 1 ml of sterile gum arabic solution prior to inoculation. Seed lots used for inoculation with PVP VA-S-630-containing inoculants (prepared as described in Example 2, $2.2 \times 10^{10}$ rhizobia $g^{-1}$) were pre-moistened with 0.1 ml of sterile water. The seed lots were transferred to irradiated polythene bags which were sealed and held at laboratory temperature for six months. At intervals, 50 seed lots were removed from each treatment an the viable rhizobial cells per seed determined (see Table 2).

TABLE 2

| Time after inoculation (months) | No. Rhizobia per seed | | |
|---|---|---|---|
| | Dry Inoculation | Gum Arabic Slurry Inoculation | Inoculation with PVP-VA-S-630-containing inoculant |
| 0 | 85,000 | 3,100,000 | 3,400,000 |
| 3 | N.D. | 94,000 | 190,000 |

TABLE 2-continued

| Time after inoculation (months) | No. Rhizobia per seed | | |
|---|---|---|---|
| | Dry Inoculation | Gum Arabic Slurry Inoculation | Inoculation with PVP-VA-S-630-containing inoculant |
| 6 | N.D. | N.D. | 760 |

N.D. Not detected

The results in Table 2 show that in this Example, both slurry inoculation of seeds with gum arabic and moist inoculation with PVP-VA-S-630 inoculant achieve the desired number of rhizobia per seed (i.e. in excess of $10^5$ per seed). Dry inoculation with conventional inoculation was unsatisfactory. However in all cases, the number of rhizobia per seed fell below $10^5$ within 3–6 months of storage, even though the coated seeds were stored in bags.

EXAMPLE 4

PVP-VA-S-630 clearly promotes the survival of rhizobia on the seed surface so it was of interest to determine if increased concentrations of PVP-VA-S-630 in peat inoculants would improve rhizobial survival to a degree sufficient to given an adequate shelf-life.

Packs of peat based inoculants containing 0, 5, 10 and 15 g of PVP-VA-S-630 were prepared as described in Example 2. It is not possible to prepare 150 g peat packs containing greater than 15 g of PVP-VA-S-630 because this leads to agglomeration of peat particles, thus making seed coating ineffective.

The inoculants were used to inoculate soybean seeds in two ways:

| 1. | Moist - 300 g of seed were slightly moistened with 0.4 ml of water, prior to mixing with 1 g of inoculant. |
|---|---|
| 2. | Slurry - 1 g of inoculant was slurried with 2 ml of water and then mixed with 300 g of seed. |

Inoculated seeds were held at room temperature for 30 minutes prior to removal of unadhered inoculant by sieving. The seeds were then exposed to air and held at room temperature for 1 hour prior to determination of rhizobial numbers per seed. The results are presented in Table 3.

The results show that by increasing the PVP-VA-S-630 content of peat inoculatns to the maximum possible level, the desired number of rhizobia per seed (i.e. in excess of $10^5$ per seed) is achievable but that further improvement is desirable.

TABLE 3

| PVP-VA-S-630 Content of Inoculant (g) | No. Rhizobia per g inoculant | No. Rhizobia per seed | |
|---|---|---|---|
| | | Moist Inoculation | Slurry Inoculation |
| 0 | $1.4 \times 10^{10}$ | $3.1 \times 10^4$ | $3.1 \times 10^4$ |
| 5 | $2.3 \times 10^9$ | $6.5 \times 10^4$ | $1.0 \times 10^5$ |
| 10 | $1.2 \times 10^{10}$ | $3.6 \times 10^5$ | $8.1 \times 10^5$ |
| 15 | $2.5 \times 10^9$ | $8.0 \times 10^4$ | $1.3 \times 10^5$ |

EXAMPLE 5

Pre-inoculation of soybean seeds 2 g of peat-based inoculant containing PVP-VA-S-630 (prepared as in Example 2) were mixed with 3 ml of an aqueous suspension of PVP-VA-S-630 (10, 20, or 30% w/w) at room temperature. The suspension was slurried with 300 g of soybean seeds and the slurry allowed to air dry. The seed lots were transferred to irradiated polythene bags which were sealed and held at room temperature for five months. At intervals, 50 seed lots were removed from each treatment an the viable rhizobial cells per seed determined (see Table 4).

The effect of varying the amount of peat-based inoculant was studied. 2, 3, 4 or 5 g of inoculant was mixed with 3, 4, 4 or 5 ml of PVP-VA-S-630 suspension respectively. When 3 or 4 g of inoculant was used, 1 ml of water was also added to the mixture. When 5 g of inoculant was used, 2 ml of water was added to the mixture. The suspensions were slurried with seeds, dried, bagged and viable rhizobial cells determined as described above (see Table 4).

Peat-clay inoculants containing PVP-VA-S-630 (prepared as described in Example 2) were used instead of peat-based inoculants, and pre-inoculated soybean seeds were prepared as described above. Viable rhizobial cells per seed were determined (see Table 5).

Peat-based inoculants containing PVP-VA-S-630 and one of three different B. japonicum strains, RCR 3407 (CB 1809), 532c and G49, were used to pre-inoculate soybean seeds as described above and viable rhizobial cells per seed determined (see Table 4).

TABLE 4

| | | Viable Rhizobial Cells Per seed Storage Period (Months) | | | |
|---|---|---|---|---|---|
| | | 0 | 1 | 3 | 5 |
| Strain RCR 3407 (peat inoculant) | | | | | |
| a) 2 g inoculant | 10% PVP-VA-S630 | $9.5 \times 10^5$ | $1.2 \times 10^5$ | $2.0 \times 10^5$ | $1.0 \times 10^5$ |
| | 20% PVP-VA-S630 | $4.1 \times 10^5$ | $6.8 \times 10^5$ | $3.8 \times 10^5$ | $1.7 \times 10^5$ |
| | 30% PVP-VA-S630 | $2.8 \times 10^5$ | $5.4 \times 10^5$ | $3.6 \times 10^5$ | $1.4 \times 10^5$ |
| b) 3 g inoculant | 10% PVP-VA-S630 | $3.0 \times 10^6$ | $4.7 \times 10^5$ | $2.1 \times 10^5$ | $1.3 \times 10^5$ |
| | 20% PVP-VA-S630 | $1.1 \times 10^6$ | $5.4 \times 10^5$ | $4.3 \times 10^5$ | $2.1 \times 10^5$ |
| | 30% PVP-VA-S630 | $1.6 \times 10^6$ | $7.8 \times 10^5$ | $4.5 \times 10^5$ | $2.3 \times 10^5$ |
| c) 4 g inoculant | 10% PVP-VA-S630 | $2.9 \times 10^6$ | $2.7 \times 10^6$ | $6.0 \times 10^5$ | $2.2 \times 10^5$ |
| | 20% PVP-VA-S630 | $2.6 \times 10^6$ | $1.7 \times 10^6$ | $7.1 \times 10^5$ | $4.1 \times 10^5$ |
| | 30% PVP-VA-S630 | $3.2 \times 10^6$ | $1.5 \times 10^6$ | $6.8 \times 10^5$ | $3.4 \times 10^5$ |
| d) 5 g inoculant | 10% PVP-VA-S630 | $2.0 \times 10^6$ | $1.1 \times 10^6$ | $5.6 \times 10^5$ | $3.4 \times 10^5$ |
| | 20% PVP-VA-S630 | $2.2 \times 10^6$ | $7.3 \times 10^5$ | $6.1 \times 10^5$ | $4.1 \times 10^5$ |
| | 30% PVP-VA-S630 | $3.0 \times 10^6$ | $6.5 \times 10^5$ | $6.0 \times 10^5$ | $4.5 \times 10^5$ |
| Strain 532c (peat inoculant) | | | | | |
| a) 2 g inoculant | 20% PVP-VA-S630 | $4.5 \times 10^6$ | $2.6 \times 10^6$ | $6.0 \times 10^5$ | $4.7 \times 10^5$ |
| b) 4 g inoculant | 20% PVP-VA-S630 | $3.0 \times 10^6$ | $1.3 \times 10^6$ | $8.4 \times 10^5$ | $5.0 \times 10^5$ |
| " | 30% PVP-VA-S630 | $3.4 \times 10^6$ | $6.3 \times 10^5$ | $6.4 \times 10^5$ | $5.1 \times 10^5$ |
| Strain G49 (peat inoculant) | | | | | |
| a) 2 g inoculant | 20% PVP-Va-S630 | $4.2 \times 10^6$ | $8.6 \times 10^5$ | $1.0 \times 10^5$ | $0.5 \times 10^5$ |
| b) 4 g inoculant | 20% PVP-Va-S630 | $8.0 \times 10^6$ | $5.8 \times 10^5$ | $3.0 \times 10^5$ | $1.0 \times 10^5$ |
| " | 30% PVP-Va-S630 | $6.8 \times 10^6$ | $8.4 \times 10^5$ | $3.1 \times 10^5$ | $1.4 \times 10^5$ |

TABLE 5

| | | Viable Rhizobial Cells Per seed Storage Period (Months) | | | |
|---|---|---|---|---|---|
| | | 0 | 1 | 3 | 5 |
| Strain RCR 3407 (75% peat-25% clay inoculant) | | | | | |
| a) 2 g inoculant | 10% PVP-VA-S630 | $1.2 \times 10^6$ | $2.9 \times 10^6$ | $3.0 \times 10^5$ | $1.2 \times 10^5$ |
| " | 20% PVP-VA-S630 | $2.1 \times 10^6$ | $2.6 \times 10^6$ | $4.9 \times 10^5$ | $2.7 \times 10^5$ |
| " | 30% PVP-VA-S630 | $2.8 \times 10^6$ | $2.0 \times 10^6$ | $3.6 \times 10^5$ | $2.4 \times 10^5$ |
| b) 4 g inoculant | 10% FVP-VA-S630 | $2.1 \times 10^6$ | $1.2 \times 10^6$ | $7.0 \times 10^5$ | $3.0 \times 10^5$ |
| " | 20% PVP-VA-S630 | $4.7 \times 10^6$ | $1.0 \times 10^6$ | $7.6 \times 10^5$ | $3.4 \times 10^5$ |
| " | 30% PVP-VA-S630 | $3.6 \times 10^6$ | $1.1 \times 10^6$ | $6.9 \times 10^5$ | $3.7 \times 10^5$ |
| Strain RCR 3407 (50% peat - 50% clay inoculant) | | | | | |
| a) 2 g inoculant | 10% PVP-VA-S630 | $2.4 \times 10^6$ | $5.1 \times 10^5$ | $1.8 \times 10^5$ | $0.4 \times 10^5$ |
| " | 20% PVP-VA-S630 | $3.8 \times 10^6$ | $5.9 \times 10^5$ | $2.0 \times 10^5$ | $0.9 \times 10^5$ |

The results in Tables 4 and 5 demonstrate that the target of $10^5$ rhizobia per seed can be achieved, and that the coated seeds so produced have a shelf-life in excess of 5 months.

From these results it can be concluded that 10 or 20% w/w PVP-VA-S-630 suspensions are optimal and that 2–4 g of inoculant per 300 g soybean seeds (i.e. an inoculation rate of 0.7–1.3%) gives adequate viable rhizobial cells per seed after 5 months storage. The method is applicable to a range of B. japonicum strains.

EXAMPLE 6

Pre-inoculation of lucerne seeds 100 g of lucerne seeds were pre-inoculated with peat-based inoculant containing PVP-VA-S-630 and R. meliloti RCR 2001 as described in Example 5. Treated seeds were bagged and stored as described in Example 5. At intervals, viable Rhizobial cells per seed were determined (see Table 6).

TABLE 6

| | | Viable Rhizobial Cells Per Seed Storage Period (Months) | | | |
|---|---|---|---|---|---|
| | | 0 | 1 | 3 | 6 |
| a 1 g inoculant | 10% PVP-VA-S630 | $3.6 \times 10^4$ | $9.7 \times 10^3$ | $3.0 \times 10^3$ | $2.4 \times 10^3$ |
| " | 20% PVP-VA-S630 | $4.0 \times 10^4$ | $1.8 \times 10^4$ | $8.0 \times 10^3$ | $4.0 \times 10^3$ |

TABLE 6-continued

|  |  | Viable Rhizobial Cells Per Seed Storage Period (Months) | | | |
|---|---|---|---|---|---|
|  |  | 0 | 1 | 3 | 6 |
| " | 30% PVP-VA-S630 | $5.2 \times 10^4$ | $1.9 \times 10^4$ | $7.4 \times 10^3$ | $4.0 \times 10^3$ |
| b) 1.5 g inoculant | 10% PVP-VA-S630 | $8.7 \times 10^4$ | $2.4 \times 10^4$ | $1.0 \times 10^4$ | $5.1 \times 10^3$ |
| " | 20% PVP-VA-S630 | $6.1 \times 10^4$ | $3.1 \times 10^4$ | $2.1 \times 10^4$ | $4.3 \times 10^3$ |
| " | 30% PVP-VA-S630 | $10.0 \times 10^4$ | $3.2 \times 10^4$ | $2.0 \times 10^4$ | $6.0 \times 10^3$ |
| c) 2 g inoculant | 10% PVP-VA-S630 | $9.5 \times 10^4$ | $2.8 \times 10^4$ | $2.0 \times 10^4$ | $5.8 \times 10^3$ |
| " | 20% PVP-VA-S630 | $8.2 \times 10^4$ | $3.6 \times 10^4$ | $2.4 \times 10^4$ | $6.2 \times 10^3$ |
| " | 30% PVP-VA-S630 | $1.0 \times 10^5$ | $4.6 \times 10^4$ | $2.8 \times 10^4$ | $7.1 \times 10^3$ |

The results in Table 6 demonstrate that the target of $10^3$ rhizobia per lucerne seed can be achieved, and that the coated seeds so produced have a shelf-life in excess of 6 months.

From these results it can be concluded that 10 or 20% w/w PVP-VA-S-630 suspensions are optimal and that 1.5-2 g of inoculant per 100 g lucerne seeds (i.e. an inoculation rate of 1.5-2%) achieves the target of $1 \times 10^3$ viable Rhizobial cells per seed after 6 months storage.

EXAMPLE 7

Pre-inoculation of clover seeds 100 g of white clover seeds were pre-inoculated with peat-based inoculant containing PVP-VA-S-630 and *R. leguminosarum* biovar trifolii TA1 as described in Example 5. Treated seeds were bagged and stored as described in Example 5. At intervals, viable Rhizobial cells per seed were determined (see Table 7).

The results in Table 7 demonstrate that $10^3$ rhizobia per clover seed can be achieved, and that the coated seeds so produced have a shelf-life in excess of 3 months.

TABLE 7

|  |  | Viable Rhizobial Cells Per Seed Storage Period (Months) | | |
|---|---|---|---|---|
|  |  | 0 | 1 | 3 |
| a) 1 g inoculant | 10% PVP-VA-S630 | $2.6 \times 10^3$ | $7.9 \times 10^4$ | $4.0 \times 10^3$ |
| " | 20% PVP-VA-S630 | $3.0 \times 10^3$ | $8.8 \times 10^4$ | $6.8 \times 10^3$ |
| " | 30% PVP-VA-S630 | $5.0 \times 10^3$ | $6.3 \times 10^4$ | $6.0 \times 10^3$ |
| b) 2 g inoculant | 20% PVP-VA-S630 | $3.8 \times 10^3$ | $3.6 \times 10^4$ | $7.4 \times 10^3$ |

EXAMPLE 8

2 g of peat-based *B. japonicum* inoculant were containing PVP-VA-S-630 (prepared as in Example 2) were mixed with 3 ml of a 20% w/w PVP-VA-S-630 aqueous suspension at room temperature. The suspension was slurried with 300 g of soybean seeds and the slurry dusted with 9 kg of Surrey Powder. After air drying, the seed lots were transferred to irradiated polythene bags which were sealed and stored at room temperature. At intervals, 50 seed lots were removed and viable rhizobial cells per seed determined (see Table 8).

TABLE 8

| Storage Period (Months) | Viable Rhizobial Cells Per Seed |
|---|---|
| 0 | $4.6 \times 10^6$ |
| 2 | $6.0 \times 10^5$ |
| 4 | $3.4 \times 10^5$ |

EXAMPLE 9

2 g of peat-based *B. japonicum* inoculant were containing PVP-VA-S-630 (prepared as in Example 2) were mixed with 4.2 ml of a 20% w/w PVP-VA-S-630 suspension containing 0.12 g of the dyes Rhodamine B500 or Blue 23123. The suspension was slurried with 300 g of soybean seeds and the slurry air-dried. Seed lots were transferred to irradiated polythene bags which were sealed and stored at room temperature. At intervals, 50 seed lots were removed and viable rhizobial cells per seed determined (see Table 9).

TABLE 9

| Storage Period (Months) | Viable Rhizobial Cells Per Seed | |
|---|---|---|
|  | Rhodamine B500 | Blue 23123 |
| 0 | $3.8 \times 10^6$ | $3.8 \times 10^6$ |
| 2 | $5.1 \times 10^5$ | $5.4 \times 10^5$ |
| 4 | $2.2 \times 10^5$ | $3.1 \times 10^5$ |

EXAMPLE 10

2 g of peat-based *B. japonicum* inoculant were containing PVP-VA-S-630 (prepared as in Example 2) were mixed with 4.2 ml of a 20% w/w PVP-VA-S-630 aqueous suspension containing 0.6 g of the titanium dioxide-coated mica (lustre) 100 Silver Pearl. The suspension was slurried with 300 g of soybean seeds and the slurry air-dried. Seed lots were transferred to irradiated polythene bags which were sealed and stored at room temperature. At intervals, 50 seed lots were removed and viable rhizobial cells per seed determined (see Table 10).

TABLE 10

| Storage Period (Months) | Viable Rhizobial Cells Per Seed |
|---|---|
| 0 | $3.9 \times 10^6$ |
| 2 | $4.4 \times 10^5$ |
| 4 | $2.6 \times 10^5$ |

EXAMPLE 11

2 g of peat-based *B. japonicum* inoculant were containing PVP-VA-S-630 (prepared as described in Example 2) were mixed with 4.2 ml of a 20% w/w PVP-VA-S-630 suspension containing 0.12 g of either Rhodamine B500 or Blue 23123 and 6 g of 100 Silver Pearl. The suspension was slurried with 300 g of soybean seeds and the slurry air-dried. Seed lots were transferred to irradiated polythene bags which were sealed and stored at room temperature. At intervals, 50 seed lots were removed and viable rhizobial cells per seed determined (see Table 11).

TABLE 11

| Storage Period Months | Viable Rhizobial Cells Per Seed | |
|---|---|---|
| | Blue 23123 | Rhodamine B500 |
| 0 | $2.8 \times 10^6$ | $3.4 \times 10^6$ |
| 2 | $2.8 \times 10^5$ | $3.0 \times 10^5$ |
| 4 | $2.3 \times 10^5$ | $2.1 \times 10^5$ |

EXAMPLE 12

Selection of fungicide-tolerant rhizobial strains

Fungicide-tolerant strains were prepared by the method of Rennie, R. J., Selection for captan tolerance in the Rhizobium phaseoli-Phaseolus vulgaris L.$N_2$-fixing symbiosis., Can. J. Soil. Sci., 1986, 66:143–150. Pure cultures of R. meliloti RCR 2001 were transferred to TY medium Beringer, J. E., R-factor transfer in Rhizobium leguminosarium, J. Gen. Microbiol., 1974, 84:188–198 to which 0, 20, 40, 60, 100 or 500 ppm of metalaxyl had been incorporated. Strains were considered tolerant if they could multiply in the presence of 100 ppm metalaxyl, immune if they could tolerate 500 ppm metalaxyl. Spontaneous mutants exhibiting growth within 14 days were recultured on TY medium without metalaxyl and then replated on TY medium containing metalaxyl in increasing concentrations. This procedure was repeated three times over the course of 1 year to ensure the genetic stability of the observed tolerance to metalaxyl.

The same procedure was followed to obtain mutants of B. japonicum RCR 3407 resistant to both carbathiin and thiram.

EXAMPLE 13

Peat-based inoculants containing PVP-VA-S-630 and metalaxyl-tolerant R. meliloti strains or carbathiin and thiram-tolerant B. japonicum strains were prepared as described in Example 2.

2 g of R. meliloti inoculant were mixed with 3 ml of an aqueous 20% w/w suspension of PVP-VA-S-630 containing 0.126 g of Apron FL TM (contains 28.35% metalaxyl, supplier Gustafson). The suspension was slurried with 100 g of lucerne seeds and the slurry air-dried.

2 g of B. japonicum inoculant were mixed with 42 ml of an aqueous 20% w/w suspension of PVP-VA-S-630 containing 1.8 ml of Anchor TM (contains 66.7 g per liter of carbathiin and 66.7 g per liter of thiram, supplier Uniroyal). The suspension was slurried with 300 g of soybean seeds and the slurry air-dried.

Seed lots were transferred to irradiated polythene bags which were sealed and stored at room temperature. At intervals, 50 seed lots were removed and viable rhizobial cells per seed determined (see Table 12).

TABLE 12

| Storage Period (Months) | Viable Rhizobial Cells Per Seed | |
|---|---|---|
| | R. meliloti | B. japonicum |
| 0 | $7.5 \times 10^4$ | $4.3 \times 10^5$ |
| 2 | $3.2 \times 10^4$ | $3.1 \times 10^5$ |
| 4 | $8.1 \times 10^3$ | $2.2 \times 10^5$ |

EXAMPLE 14

The same procedure to pre-inoculate soybean seeds as described in Example 5 can be used with any of the following polymers substituting for PVP-VA-S-630: poly (methyl vinyl ether) maleic anhydride copolymers, free acids of the copolymer of methyl vinyl ether and maleic anhydride, vinyl pyrrolidone/styrene copolymers, partially hydrolysed polyvinylalcohols, vinyl acetate/butyl acrylate copolymers, vinylacetate homopolymers, vinyl acetate/VeoVa 10/butyl acrylate terpolymers, acrylic copolymers, styrene/acrylic ester copolymers, vinyl acetate/ethylene copolymers and polyvinyl acetate.

EXAMPLE 15

Lucerne seeds were coated with R. meliloti and the dye Blue 23123 using the method described in Example 7, Five months after coating the seeds were sown in a field trial and growth of the resulting plants compared with that of plants resulting from untreated seeds. Ten weeks after sowing, the plants from a 40 cm length of row were cut and the weight of plant tops measured (Table 13). Pre-inoculation of lucerne seed with R. meliloti resulted in increased plant growth.

TABLE 13

| | % Increase in Plant Tops Weight* |
|---|---|
| Site 1 | 39 |
| Site 2 | 59 |

*Compared to uninoculated seeds

EXAMPLE 16

Soybean seeds were coated with B. japonicum and the dye Rhodamine B500 using the method described in Example 9. Three months after coating the seeds were sown in a field. The trial was taken to harvest and nodule number and weight plus seed yield measured (Table 14). Pre-inoculation of soybean seed with B. japonicum resulted in increased seed yield, nodule number and weight compared to uninoculated seeds.

TABLE 14

| | Nodule Number (average of 10 plants) | Nodule Fresh Weight (g per 10 plants) | Seed Yield (bushel/acre) |
|---|---|---|---|
| Uninoculated | 0.3 | 3.5 | 36.1 |
| Pre-inoculated | 30.0 | 9.4 | 51.8 |

I claim:

1. A soybean seed coated with an inoculant composition comprising a carrier medium, a microorganism having a beneficial effect on the seed or resulting plant, and an adhesive polymeric material, said seed having an average loading of at least $10^5$ viable organisms per seed, which loading is maintained under conditions of storage in a sealed irradiated polythene bag at room temperature for at least five months, and wherein:

said carrier is selected from the group consisting of peat, vermiculite, clay, silt, graphite, talc, filter mud, coir dust, bagasse, composted corn cobs, and coal dust;

said adhesive polymer is selected from the group consisting of copolymers of vinyl pyrrolidone, and vinyl acetate, poly (methyl vinyl ether), maleic anhydride copolymers, free acids of the copolymer of methyl vinyl ether and maleic anhydride, vinyl pyrrolidone/styrene copolymers, partially hydrolyzed polyvinyl alcohols, vinyl acetate/butyl acrylate copolymers, vinyl acetate homopolymers, acrylic copolymers, styrene/acrylic ester copolymers, vinyl acetate/ethylene copolymers and polyvinyl acetate; and said microorganism is selected from the group consisting of bacteria of the genera Rhizobium, Pseudomonas, Serratia, Bacillus, Pasteuria, Azotobacter, Enterobacter, Azospirillum, Cyanobacteria, fungi of the genera Gliocladium, Trichoderma, Coniotherium, Verticillium, Paecilomyces, Metarhizium, mycorrhizal fungi and entomophilic nematodes.

2. The soybean seed of claim 1, wherein at least one pigment is incorporated into the coating.

3. The soybean seed of claim 1, wherein the fungicide is incorporated into the coating, and wherein said microorganism is resistant to said fungicide.

4. The soybean seed of claim 3, wherein said fungicide is selected from the group consisting of metalaxyl, carbathiin and thiram.

5. The soybean seed of claim 1, wherein said adhesive polymer is a copolymer of vinyl pyrrolidone and vinyl acetate with respective proportions by weight of 50:50 to 70:30.

6. The soybean seed of claim 1, wherein said carrier is peat.

7. The soybean seed of claim 1, wherein said microorganism is selected from the group consisting of *B. japonicum, R. meliloti* and *R. leguminosarum*.

8. The soybean seed of claim 1, which is prepared by applying about 2 to 4 g. of seed inoculant composition per about 300 g. of soybean seeds.

9. A lucerne seed coated with an inoculant composition comprising a carrier medium, a microorganism having a beneficial effect on the seed or resulting plant, and an adhesive polymeric material, said seed having an average loading of at least 10 viable organisms per seed, which loading is maintained under conditions of storage in a sealed irradiated polythene bag at room temperature for at least six months, and wherein said carrier is selected from the group consisting of peat, vermiculite, clay, silt, graphite, talc, filter mud, coir dust, bagasse, composted corn cobs, and coal dust;

said adhesive polymer is selected from the group consisting of copolymers of vinyl pyrrolidone, and vinyl acetate, poly (methyl vinyl ether), maleic anhydride copolymers, free acids of the copolymer of methyl vinyl ether and maleic anhydride, vinyl pyrrolidone/styrene copolymers, partially hydrolyzed polyvinyl alcohols, vinyl acetate/butyl acrylate copolymers, vinyl acetate homopolymers, acrylic copolymers, styrene/acrylic ester copolymers, vinyl acetate/ethylene copolymers and polyvinyl acetate; and said microorganism is selected from the group consisting of bacteria of the genera Rhizobium, Pseudomonas, Serratia, Bacillus, Pasteuria, Azotobacter, Enterobacter, Azospirillum, Cyanobacteria, fungi of the genera Gliocladium, Trichoderma, Coniotherium, Verticillium, Paecilomyces, Metarhizium, mycorrhizal fungi and entomophilic nematodes.

10. The lucerne seed of claim 9, wherein at least one pigment is incorporated into the coating.

11. The lucerne seed of claim 9, wherein a fungicide is incorporated into the coating, and wherein said microorganism is resistant to said fungicide.

12. The lucerne seed of claim 11, wherein said fungicide is selected from the group consisting of metalaxyl, carbathiin and thiram.

13. The lucerne seed of claim 9, wherein said adhesive polymer is a copolymer of vinyl pyrrolidone and vinyl acetate with respective proportions by weight of 50:50 to 70:30.

14. The lucerne seed of claim 9, wherein said carrier is peat.

15. The lucerne seed of claim 9, wherein said microorganism is selected from the group consisting of *B. japonicum, R. meliloti* and *R. leguminosarum*.

16. The lucerne seed of claim 9, which is prepared by applying about 1.5 to 2 g of said inoculant composition per about 100 g of lucerne seeds.

17. A clover seed coated with an inoculant composition comprising a carrier medium, a microorganism having a beneficial effect on the seed or resulting plant, and an adhesive polymeric material, said seed having an average loading of at least 10 viable organisms per seed, which loading is maintained under conditions of storage in a sealed irradiated polythene bag at room temperature for at least three months, and wherein:

said carrier is selected from the group consisting of peat, vermiculite, clay, silt, graphite, talc, filter mud, coir dust, bagasse, composted corn cobs, and coal dust, said adhesive polymer is selected from the group consisting of copolymers of vinyl pyrrolidone and vinyl acetate, poly (methyl vinyl ether), maleic anhydride copolymers, free acids of the copolymer of methyl vinyl ether and maleic anhydride, vinyl pyrrolidone/styrene copolymers, partially hydrolysed polyvinyl alcohols, vinyl acetate/butyl acrylate copolymers, vinyl acetate homopolymers, acrylic copolymers, styrene/acrylic ester copolymers, vinyl acetate/ethylene copolymers and polyvinyl acetate; and said microorganism is selected from the group consisting of bacteria of the genera Rhizobium, Pseudomonas, Serratia, Bacillus, Pasteuria, Azotobacter, Enterobacter, Azospirillum, Cyanobacteria, fungi of the genera Gliocladium, Trichoderma, Coniotherium, Verticillium, Paecilomyces, Metarhizium, mycorrhizal fungi and entomophilic nematodes.

18. The clover seed of claim 17, wherein at least one pigment is incorporated into the coating.

19. The clover seed of claim 17, wherein a fungicide is incorporated into the coating, and wherein said microorganism is resistant to said fungicide.

20. The clover seed of claim 19, wherein said fungicide is selected from the group consisting of metalaxyl, carbathiin and thiram.

21. The clover seed of claim 17, wherein said adhesive polymer is a copolymer of vinyl pyrrolidone and vinyl acetate with respective proportions by weight of 50:50 to 70:30.

22. The clover seed of claim 17, wherein said carrier is peat.

23. The clover seed of claim 17, wherein said microorganism is selected from the group consisting of *B. japonicum, R. meliloti* and *R. leguminosarum*.

24. The clover seed of claim 17, which is prepared by applying about 2 to 4 g of said inoculant composition per about 300 g of clover seeds.

* * * * *